United States Patent
Kan

[19]

[11] Patent Number: 6,106,455
[45] Date of Patent: Aug. 22, 2000

[54] RADIOACTIVE SEED VACUUM PICKUP PROBE

[76] Inventor: William C. Kan, 2000 Baker Trace, Dothan, Ala. 36303

[21] Appl. No.: 09/175,994

[22] Filed: Oct. 21, 1998

[51] Int. Cl.$^7$ .................................................. A61M 36/00
[52] U.S. Cl. .................................................................. 600/7
[58] Field of Search .......................................... 600/1–8

[56] References Cited

U.S. PATENT DOCUMENTS

| | | |
|---|---|---|
| 4,364,376 | 12/1982 | Bigham . |
| 5,120,973 | 6/1992 | Rohe et al. . |
| 5,147,282 | 9/1992 | Kan . |
| 5,342,283 | 8/1994 | Good . |
| 5,562,232 | 10/1996 | Pearson . |
| 5,716,317 | 2/1998 | Okano et al. . |

*Primary Examiner*—John P. Lacyk
*Attorney, Agent, or Firm*—Jacobson, Price, Holman & Stern, PLLC

[57] ABSTRACT

A vacuum force is applied to simplify the routine of pick-up and handling of radioactive seeds, singly or in groups, and to quickly and safely transfer the seeds into a shielded direct-coupled holding vial. The shielded holding vial is part of a hand held probe which can be detached quickly and interchanged with another empty shielded holding vial, thereby permitting the sorting or separating of radioactive seeds into different groups. Due to its quick pick-up ability, light weight and quick-coupling shielded storage vial, the spring loaded probe can greatly reduce the pick-up and transfer time and hence, eliminate radiation exposure to an individual. As a simple vacuum transfer pick-up, the spring loaded probe is provided with an adaptive mouthpiece which permits manipulation of radioactive seeds, within a shielded area. In addition, the handling of small objects including non-radioactive objects such as TLD chips commonly used in radiation or radiation measurement areas is achieved. To further eliminate radiation exposure to personnel handling loose seeds, the top portion of the hand-held spring loaded probe is made with a direct-coupling companion shielded holding vial, which acts as a receptacle to collect seeds. The shielded holding vial can be "un-coupled" quickly and easily so that multiple shielded holding vials may be used with the spring loaded probe to sort groups of radioactive seeds into several designated shielded holding vials.

20 Claims, 8 Drawing Sheets

RADIOACTIVE SEED VACUUM PICKUP PROBE

FIELD OF THE INVENTION

The present invention relates to the field of radioactive seed transport and radioactive seed assay systems.

BACKGROUND OF THE INVENTION

To comply with the American College of Radiology Quality Assurance regulations for quality control of radioactive seed activity, a minimum of 10% of radioactive seeds intended for patient usage must be assayed. To comply with these requirements, a radioactive seed is placed by long handle forceps into a plastic tray and lowered to the bottom of a well of a well calibrator or a well of a well counter. One seed at a time is lowered to and then removed from the bottom of the well.

At specific well calibrator settings for a particular nuclide, the radioactive activity is displayed and can then be recorded. This procedure results in unnecessary radioactive exposure to an individual charged with testing the seeds.

SUMMARY OF THE INVENTION

By the present invention, an apparatus is disclosed which uses a vacuum force to simplify the routine of pick-up and handling of radioactive seeds, singly or in groups, to quickly and safely transfer the seeds into a shielded direct-coupled holding vial. The shielded holding vial is part of a hand held probe which can be detached quickly and interchanged with another empty shielded holding vial, thereby permitting the sorting or separating of radioactive seeds into different groups. Due to its quick pick-up ability, light weight and quick-coupling shielded storage vial, the spring loaded probe of the present invention can greatly reduce the pick-up and transfer time and hence, eliminate radiation exposure to an individual.

As a simple vacuum transfer pick-up, the spring loaded probe is provided with an adaptive mouthpiece which permits manipulation of radioactive seeds, within a shielded area. In addition, the handling of small objects including non-radioactive objects such as TLD chips commonly used in radiation or radiation measurement areas is achieved.

To further eliminate radiation exposure to personnel handling loose seeds, the top portion of the hand-held spring loaded probe is made with a direct-coupling companion shielded holding vial, which acts as a receptacle to collect seeds. The shielded holding vial can be "un-coupled" quickly and easily so that multiple shielded holding vials may be used with the spring loaded probe to sort groups of radioactive seeds into several designated shielded holding vials.

To prevent seeds from spilling, following seed collection, a specially designed cap having vents to the ambient is placed onto the opening of the newly "un-coupled" shielded holding vial. The vented cap also allows the holding vials, with their radioactive seed contents, to be sterilized immediately following seed assay without further transfer or manipulation of the radioactive seeds, thereby further eliminating radiation exposure to personnel.

The spring loaded probe can also be very effectively used for assaying radioactive seed activity in any well chamber or well counter. The hand-held spring loaded probe has a removable adaptive mouthpiece. With the mouthpiece in place, the probe can be used as a pickup probe from outside a mini-dome shield to manipulate one seed at a time within the mini-dome shield. Each seed is picked up individually and dropped into a low friction material tube made of a compound having elements with a low atomic number such as the material marketed under the tradename TEFLON, which protrudes through the platform base of the mini-dome shield down into the well bottom of a well counter or well calibrator.

By removing the adaptive mouthpiece, the spring loaded probe can now be used as a retrieval probe capable of suctioning up multiple seeds simultaneously. As a retrieval probe, it is lowered inside the mini-dome shield to dock with the TEFLON tube funnel opening and to suction all the seeds back from the bottom of the well, up through the spring loaded probe and into a directly-coupled shielded holding vial. These shielded holding vials as mentioned previously, may then be uncoupled, closed with a special vented cap and sent for sterilization, again eliminating exposure during seed assay and simplifying the preparation of seeds for sterilization prior to loading into the needle for patient seed implantation.

A shielded viewing dome is placed on top of the well of a well calibrator or well counter and a vertically oriented TEFLON tube, with a diameter larger than a seed diameter, protrudes through a hole in the dome platform. The distal end of the TEFLON tube, having a restricted end or an opening smaller than the diameter of a seed, extends downward to the bottom of the well of the well counter or well calibrator used to measure radioactive seed activity. The restricted end holds seeds for evaluation in the well, after which the seeds are retrieved by a suction force without any exposure to personnel.

A metallic tube is slipped over the proximal end of the TEFLON tube to prevent curling of the TEFLON tube and make it straight but permits a defined segment of the distal end of the TEFLON tube to be exposed at the bottom of the well. Radioactive seeds are then emptied into the shielded dome on the dome platform, which is over and on top of the well.

Using the spring loaded probe with adaptive mouthpiece as a pickup probe or a separate, regular vacuum pickup probe, a seed is picked up and dropped into the proximal end of the TEFLON tube. By gravity, the seeds will fall to the distal end of the tube at the bottom of the well. After an activity reading is recorded, the spring loaded probe is lowered further into the shielded dome against the bias of the spring, to dock with the funneled opening of the proximal end of the TEFLON tube on the dome platform. The seed or seeds at the bottom of the TEFLON tube are immediately suctioned up into the spring loaded probe-shielded holding vial. This process is repeated until the desired number of seeds has been assayed.

The remaining seeds can also quickly be suctioned out of the dome into the directly coupled vial. At any time, a new empty shielded holding vial can be quickly exchanged so that seeds can be sorted into different vials according to their activities.

The spring loaded probe enables the active transfer of seeds into a directly coupled shielded storage vial by means of an inner and outer tube design so that seeds may be gathered up and transferred into their own shielded storage vial without physical exposure to personnel. Direct coupling of the shielded storage vial to the main body of the spring loaded probe makes it an integral part of the probe proper for seed transfer and collection.

Seed pickup time is minimized and exposure normally expected during seed transfer to a storage container is eliminated with the uni-body design. In addition, both the spring loaded probe main body and the directly coupled storage vial are designed with appropriate shielding so there is no exposure.

The vented cap of the spring loaded probe combined with a detachable shielded storage vial forms a safe shielded sterilization container. Steam from an autoclave is able to circulate to the inner radioactive seed contents by means of vents achieving high temperature; high-pressure sterilization inside the thick walled shielded vial. A high temperature nylon basket holds the seeds away from the metal wall of the vial base to assure that seeds do not clump due to moisture but are dry making needle loading easier.

The main body of the spring loaded probe consists of an inner metal tube and an outer metal tube. The upper portion of the inner tube opens to the interior of the shielded storage vial and the lower portion of the inner tube has a luer-tapered mouth forming the only entrance of the spring loaded probe. The luer-tapered mouth is intended for docking to the adaptive mouthpiece for use as a single seed manipulative pickup probe. The outer tube, between both ends of the outer tube and inner tube portion within the outer tube, is filled with ring plugs. The upper portion of the outer tube has multiple slits (only six shown) and the width of each slit is smaller than the diameter of a radioactive seed thereby allowing only vacuum to pass therethrough and preventing seeds from ever passing through the slits into the inter-tubing space.

Considering a distorted boundary line of a conceptual shielded vial illustrates the principles of a vacuum airflow path from high pressure to low pressure inside the spring loaded probe. One or more seeds are suctioned into the probe entrance and expelled at the other end, the upper portion of the inner tube, provided that the control orifice is blocked, with either a plug or the forefinger, to complete the vacuum air flow path. When the adaptive mouthpiece is not used, the control orifice is plugged.

The expelled seeds from the upper inner tube become trapped inside the nylon basket of the shielded vial. All incoming seeds will accumulate within the shielded vial while the vacuum air flow continues on through the slit opening of the outer tube and between the inner and outer tubes, in the inter-tubing space, and to the vacuum receiving port completing the vacuum flow path.

For seed implantation, the number of seeds and their activities are determined for a specific patient case. As per patient case order, a determined number of seeds of specified activities are received from the manufacturer or shipper. Upon arrival, a minimum of 10% of received seeds must be assayed to meet State and Federal regulations.

The primary objective of the spring loaded probe of the present invention in radioactive seed assay is the elimination of cumulative exposure to the user and the reduction of tedious handling time for seed assays. At present, the bare hand is used with forceps to pick up radioactive seeds and to hold the plastic tray being lowered into and retrieved from a well of a well calibrator or a well of a well counter for each seed assay.

The spring loaded probe of the present invention makes it possible to assay all of the seeds for each patient case, not merely the required 10%, within an acceptable time interval but with no exposure to the user. It is necessary to gather enough seed activity statistic samples and select the maximum number of seeds in staggered fashion for each well count with statistical certainty for the remaining seeds. With this accomplished, overall assay time is shortened and exposure is eliminated.

To accomplish this, three things are needed, a viewable shield housing the radioactive seeds, a tube confining a seed (or seeds) running from the shielded housing to the bottom of the well and the spring loaded vacuum pickup probe. The shielded mini-dome, housing the radioactive seeds, rests on top of a well of a well counter or well calibrator. A TEFLON tube whose diameter is larger than the seed diameter which extends from and through the dome platform surface reaching down to the bottom of the well.

Using a pickup probe, either the spring loaded probe or another pickup probe, one seed at a time is dropped into the TEFLON tube. The seed travels by gravity to the bottom of the tube located in the well where the activity is read. This seed (or seeds) is then retrieved with and through the spring loaded vacuum pickup probe back up and into its own directly coupled shielded storage vial.

The mini-dome shield is formed by a square tube-shaped metal piece having front and back recesses milled so that front and back lead glass plates fit flush within the square shaped metal. The top of the square is milled to accept a removable access plate. The bottom opening is fitted and fixed to a platform plate with an edge smoothed to form a recessed ring area for holding seeds on the platform plate. These seeds are introduced through the side orifice in the top access plate using a dumping funnel and dumping spout after the platform height adjustment is made.

The platform plate is attached to a rod with a lock screw for height adjustment. The rod is fastened to a ring shaped stand sitting on the top of the well, which is part of a well counter or well calibrator.

In order to send a seed (or seeds) down the well for activity reading in the TEFLON tube, the platform height must be adjusted properly with respect to the fixed ring stand on top of the well so that (1) the distal end of the TEFLON tube is located at the bottom of the well and (2) the proximal end of the TEFLON tube funnel assembly is laying flat on the platform plate of the mini-dome.

After breaking the seal and uncapping the glass vial from the manufacturer containing radioactive seeds, a dumping spout is fastened to the glass vial. Next, the dumping funnel is introduced from the top into the mini-dome shield onto the dome platform recessed ring. The seed contents of the glass vial are emptied into the dumping funnel and onto the dome platform. Both dumping funnel and spout are removed and surveyed (with GM meter) for remaining radioactivity. The radioactive seeds on the platform inside the mini-dome shield are now ready for radioactivity assay.

The vacuum pickup probe is inserted into the mini-dome shield and individual seeds are picked up and dropped into the TEFLON tube funnel opening assembly in the platform plate of the mini-dome. The funnel assembly consists of an externally threaded male top portion with a center bore shaped into a funnel and an internally threaded metal female base portion. The assembly top and base sandwich the rim of the TEFLON funnel edge in place making the initial funnel passage smooth.

A rigid metallic tube, larger than the diameter of the TEFLON tube and affixed to the base portion of the funnel assembly, extends down forming a sleeve to straighten the TEFLON tube. This metallic sleeve covers all but the exposed tip length necessary for seed activity measurement.

After an activity reading from the well by the well counter or by the well calibrator is recorded, any seed(s) inside the TEFLON tube at the bottom of the well must be retrieved back to a shielded storage vial. To retrieve the seed(s) from the TEFLON tube, a retention spring with lock ring is fitted over the probe entrance on the lower portion of the spring loaded pickup probe. With retention spring and lock ring in place, the spring loaded probe is lowered over and into the mini-dome shield through the central opening of the access plate. The retention spring passively keeps the probe in suspension directly above and away from the TEFLON tube funnel assembly while another pickup probe is used to place seeds into the TEFLON tube through the TEFLON tube funnel assembly. The position of the lock ring on the retention spring is adjusted with respect to the spring loaded pickup probe so that when force is exerted downward on the spring loaded pickup probe, the probe entrance will move down, engage fully with the top of the TEFLON tube funnel assembly and then return, with force released, to its suspended position avoiding interference for placement of the next seed(s) into the TEFLON tube.

Depressing the spring loaded pickup probe allows the probe entrance to make contact with the TEFLON tube funnel assembly. All the seeds now inside the TEFLON tube will be suctioned up simultaneously from the tip end of the tube back through the spring loaded pickup probe and into the inner nylon basket of the shielded storage vial. Normally the sequence of a) dropping a seed or seeds into the well through the TEFLON tube, b) recording seed activity from the well counter or well calibrator, and c) retrieving the seed or seeds back to the shielded vial, will be repeated many times since more than a hundred seeds are usually used per patient case. To speed up this process both hands are coordinated so that one hand picks up and drops one seed at a time with one pickup probe while the other hand presses down on the spring loaded pickup probe to retrieve the seed(s) back out of the well following recording of activity by the well counter or well calibrator.

Instead of decoupling the shielded storage vial from the main body of the spring loaded probe and coupling a different shielded vial to pick up any rejected seed(s) or to separate seeds into groups, a second spring loaded probe dedicated as a spare will further speed up the seed assay procedure. All the seeds, including those not assayed, are returned to the spring loaded probe and accumulated in the shielded storage vial. With the spring loaded probe removed from the mini-dome and inverted so that the shielded vial sits on its base, the shielded vial is uncoupled from the main body of the probe and the vented cap is placed into the shielded vial. The vented cap consists of a tube having multiple slits (only six shown) similar to the design of the upper portion of the outer tube of the spring loaded probe. The width of each slit is smaller than the diameter of a radioactive seed allowing only steam to pass through and preventing seeds from ever passing through.

An inner high-temperature nylon basket located inside the shielded vial holds the seeds away from the metallic inner wall of the shielded vial for the purpose of preventing condensation or any impurity from accumulating on the seed surface which could result in clumping during the drying cycle of the autoclave. The shielded storage vial with the vented cap secured can now be autoclaved, readying the seeds for needle loading and ultimately for seed implantation.

For convenience, seeds can be transferred between shielded storage vials. A vial coupler having internal threads can be quickly coupled to the externally threaded vial opening. Another vial, without vented cap, can then be coupled to the first shielded storage vial through the vial coupler in the same manner and the contents emptied from one to the other by inversion of the vial containing the seeds.

Accordingly, it is an object of the present invention to provide an apparatus and its method of use, including a hand-held "multi-purpose" tool, the spring loaded probe for radioactive seeds, constructed with the aim of eliminating radiation exposure by reducing time for procedures and by the calculated use of shielding. As a vacuum pickup probe, the "tool" is fitted with an adaptive mouthpiece for picking up and manipulating single seeds or it may also be used without the mouthpiece for multiple seed pickup. It may be used for quick gathering of loose seeds or retrieving seeds from a hard to reach area. The spring loading of the probe enables the active transfer of seeds into a directly coupled shielded storage vial by means of an inner and outer tube design so that seeds may be gathered up and transferred into their own shielded storage vial without physical exposure to personnel. Direct coupling of the shielded storage vial to the main body of the spring loaded probe makes it an integral part of the probe proper for seed transfer and collection. Seed pickup time is minimized and exposure normally expected during seed transfer to a storage container is eliminated with the uni-body design. In addition, both the spring loaded main body and the directly coupled storage vial are designed with appropriate shielding so there is no exposure. Because the shielded storage vial can be detached from and reattached to the probe quickly, easily and safely, radioactive seeds can be separated by activity into multiple shielded storage vials. The spring loaded probe can sort radioactive seeds into groups as determined by their measured activity in a well of a well calibrator or well counter. A specially designed vented cap combined with detachable shielded storage vial forms a safe shielded sterilization container. Steam from an autoclave is able to circulate to the inner radioactive seed contents by means of vents achieving high temperature, high-pressure sterilization inside the thick walled shielded vial. A high temperature nylon basket holds the seeds away from the metal wall of the vial base to assure that seeds do not clump due to moisture but are dry making needle loading easier.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 1A is a schematic sectional view of the main body of the spring loaded probe. The shielded storage vial is not shown so that an enlarged view of the upper portion of the inner tube and the upper portion of the outer tube having multiple slits (FIG. 1C) can be seen readily as well as a cross sectional view (FIG. 1B) taken along line 1B—1B of FIG. 1A. The shielded storage vial top having an external thread is coupled to the main body by the internal thread of the integrating coupler. The spring loaded probe can be used as a simple pickup probe with the attachment of the adaptive mouthpiece (FIG. 1D). The diameter of the tube of the adaptive mouthpiece is smaller than the seed diameter so one single seed at a time can be effectively manipulated by lifting by a vacuum force without entering the mouthpiece. The entrance diameter of the spring loaded probe is much larger than the seed diameter so that a whole group of seeds can be transported all at once. The pickup probe vacuum can be controlled with a finger tip blocking the central orifice so that vacuum is activated at the pickup probe tip.

FIG. 2 is a sectional as well as conceptual drawing of the spring loaded probe. The conceptual boundary line of the shielded storage vial encloses the opening of the internally threaded integrating coupler so that the vacuum airflow path can be easily followed. The inner and outer tubes are constructed so that the vacuum airflow continues in the inter-tubing space but not seeds. All the seeds or any object larger than the outer tubing slit width will be trapped outside of the upper portion of the outer tube and inside the shielded storage vial. The vacuum control orifice will be plugged when the adaptive mouthpiece is not used with the spring loaded probe.

FIG. 3 is a cross-sectional view of a complete spring loaded probe, without the spring. A flexible hose connected to the vacuum source (or vacuum pump) is also connected to the vacuum receiving port. The vial wall is sufficiently thick to serve as a radiation shield. The vial is constructed in two parts, the vial top and vial base, so that when disassembled, the inside wall of the vial can be visually inspected and surveyed with a Geiger-Mueller (GM) meter. It also allows replacement of the inner, high temperature nylon basket if needed. The "O" rings assure that vial tops and bases couple tightly and the nylon basket is locked in place eliminating any gaps where the seeds might get caught. When all intended radioactive seeds are accumulated in the shielded storage vial, the vial can then be detached from the main body for autoclaving. The high temperature nylon basket is used here so that radioactive seeds within the autoclaved vial will be dry and free of residual substances that can cause clumping.

A straight metallic tube forms a sleeve over the TEFLON tube guiding the TEFLON tube straight down to the bottom of the well. The tip end of the TEFLON tube is without the metallic tube sleeve so seed assay is possible. The distal unplugged tip of the TEFLON tube is smaller than the diameter of the seeds so that a seed or seeds will rest there. After a radioactivity reading is obtained from the well counter or well calibrator located at the bottom of the well, the spring loaded probe is used to actively retrieve the seed or seeds from the distal end of the TEFLON tube tip at the bottom of the well. A retention spring with lock ring is fitted over the spring loaded probe entrance and suspends the probe over and inside the top of the mini-dome shield through the top access plate. The retention spring lock ring sets the spring loaded probe position height within the mini-dome shield so that 1) there is no interference with seed manipulation when the pickup probe is being used, and 2) it allows the spring loaded probe entrance to engage properly with the TEFLON tube funnel assembly for seed retrieval. With vacuum, seed/seeds within the TEFLON tube will be suctioned up immediately from the tip end back up through the inner tube of the spring loaded probe and into the inner nylon basket of the shielded storage vial. Normally the sequence of a) dropping a seed or seeds into the well through the TEFLON tube, b) recording seed activity from the well counter or well calibrator, and c) retrieving the seed or seeds back to the spring loaded shielded vial, will be repeated many times since more than a hundred seeds are possible per patient case. To speed up this process both hands have to be coordinated so that one hand picks up and drops one seed at a time with the pickup probe while the other hand presses down on the spring loaded probe to retrieve the seed(s) back out of the well following recording of activity.

FIG. 7A is a sectional view of a shielded storage vial uncoupled from the main body. The As separated vented cap as shown in section in FIG. 7B, as taken along line 7B—7B in FIG. 7A, and shown in detail in FIG. 7C, consists of multiple slits allowing ambient air flow but preventing seeds from escaping from the vial after the vent cap is tightened. The vented shielded storage vial is constructed so that high temperature, high pressure steam from an autoclave can penetrate to the seeds while the seed contents are kept safe within the shielded vial so that there is no exposure for routine handling.

FIG. 8A is a sectional view of the vial coupler mounted on top of a vial and holding another vial for transfer of seeds. The vial coupler, as shown in side view in FIG. 8B, allows for safe, convenient seed transfer between shielded storage vials without radiation exposure.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1A:
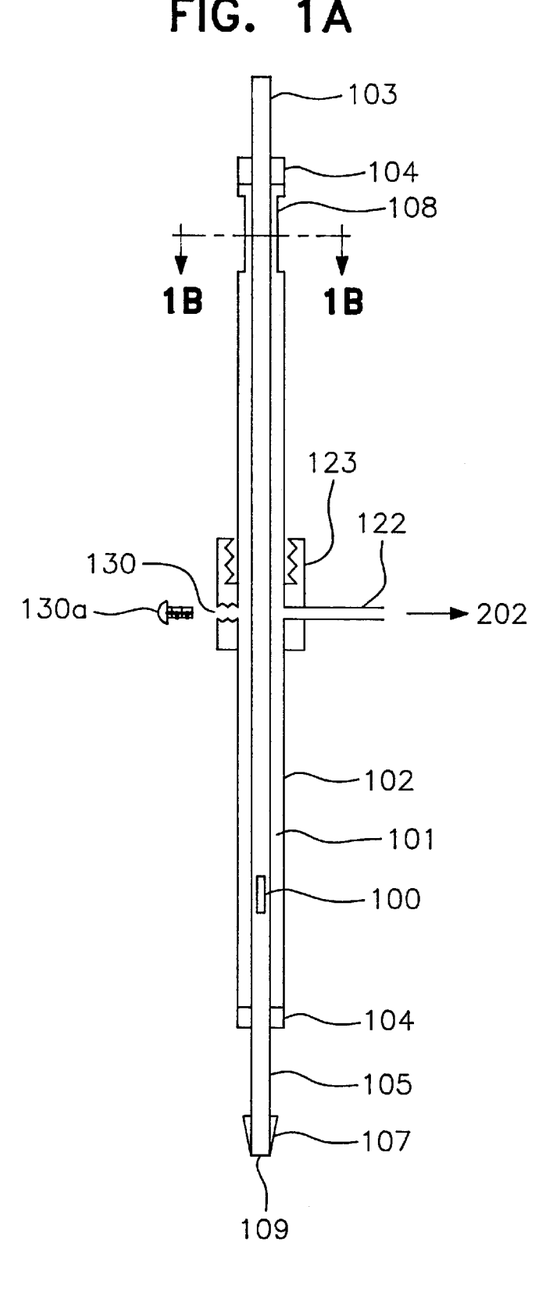
Figure 1B:
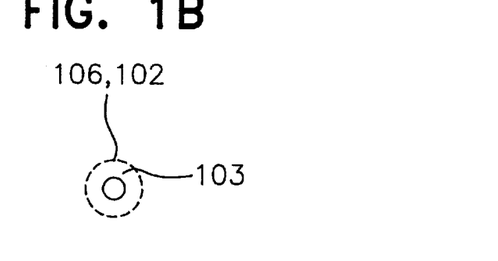
Figure 3:
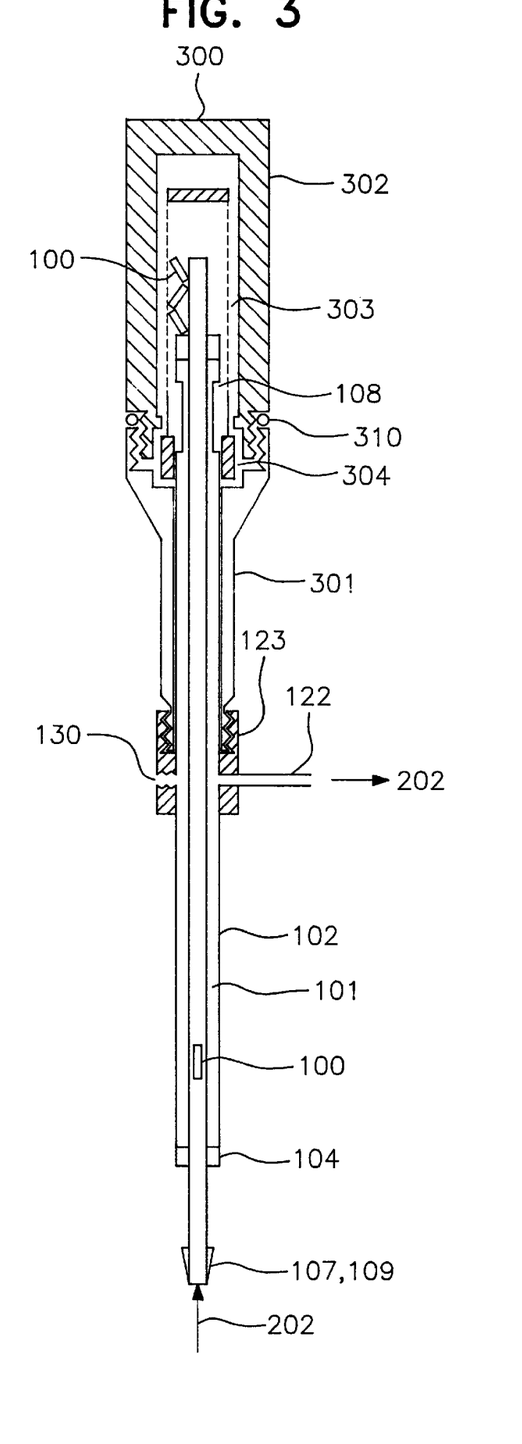

The main body of the spring loaded pickup probe consists of an inner metal tube 101 and an outer metal tube 102. The upper portion 103 of the inner tube 101 opens to the interior of a shielded storage vial 300, as shown in FIG. 3, and the lower portion 105 of the inner tube 101 has a luer-tapered mouth 107 forming the only entrance 109 to the spring loaded probe. The luer-tapered mouth 107 is intended for docking to complementary shaped luer tapered opening 107a of the adaptive mouthpiece 111 for use as a single seed manipulative pickup probe.

Figure 1C:
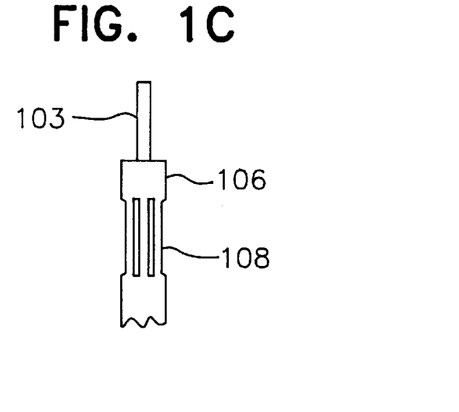
Figure 1D:
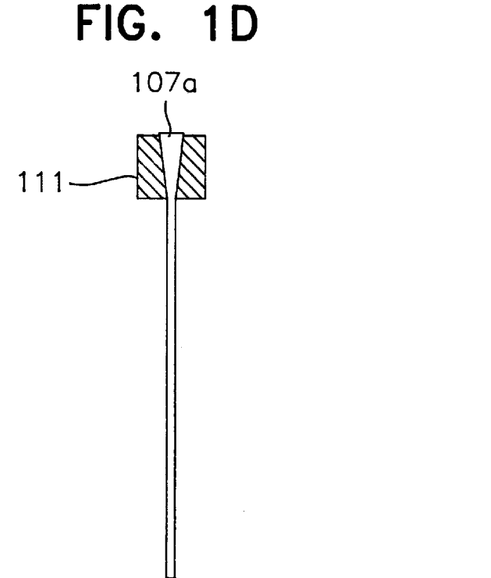

The outer tube 102, between both ends of the outer tube 102 and inner tube 101, is filled with ring plugs 104. The upper portion 106 of the outer tube 102 has multiple slits 108 (only six shown) and the width of each slit 108 is smaller than the diameter of a radioactive seed 100 thereby allowing only vacuum to pass through and preventing seeds 100 from ever passing through the slits 108 into the inter-tubing space 120.

Figure 2:
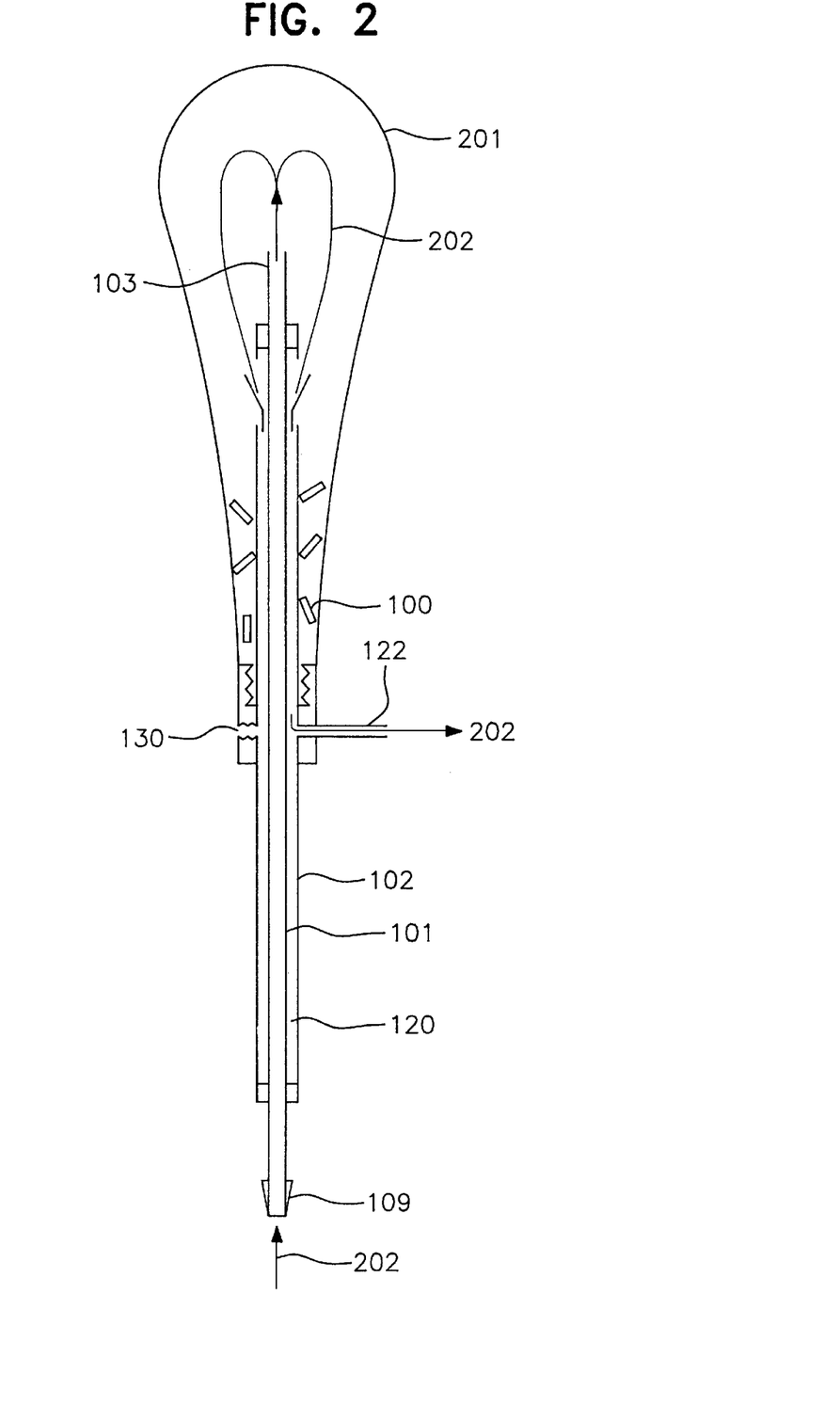

The boundary line of a shielded vial 201 is conceptually shown in FIG. 2 to illustrate the conceptual vacuum airflow path 202 from high pressure to low pressure inside the spring loaded probe. One or more seeds 100 are suctioned into the probe entrance 109 and expelled at the other end, the upper portion 103 of the inner tube 101, provided that the control orifice 130 is blocked with either a plug 130a (FIG. 1A) or the forefinger to complete the vacuum air flow path. When the adaptive mouthpiece 111 is not used, the control orifice 130 is plugged.

The expelled seeds from the upper inner tube 103 become trapped inside the nylon basket 303 of the shielded vial 300 as shown in FIG. 3. All incoming seeds 100 will accumulate within the shielded vial 300 while the vacuum air flow 202 continues on through the slit 108 opening at the upper portion 106 of the outer tube 102 and between the inner 101 and outer 102 tubes, the inter-tubing space 120 and to the vacuum receiving port 122 completing the vacuum flow path 202.

For seed implantation, the number of seeds and their activities are determined for a specific patient case. The primary objective of the spring loaded probe in radioactive seed assay is the elimination of cumulative exposure to the user and the reduction of tedious handling time for seed assays.

The spring loaded probe of the present invention makes it possible to assay all of the seeds for each patient case, not merely the required 10%, within an acceptable time interval but with no exposure. It is necessary; however, to gather enough seed activity statistic samples, and then select the maximum number of seeds in staggered fashion for each well count with statistical certainty for the remaining seeds. With this accomplished, overall assay time is shortened and exposure is eliminated.

Figure 4:
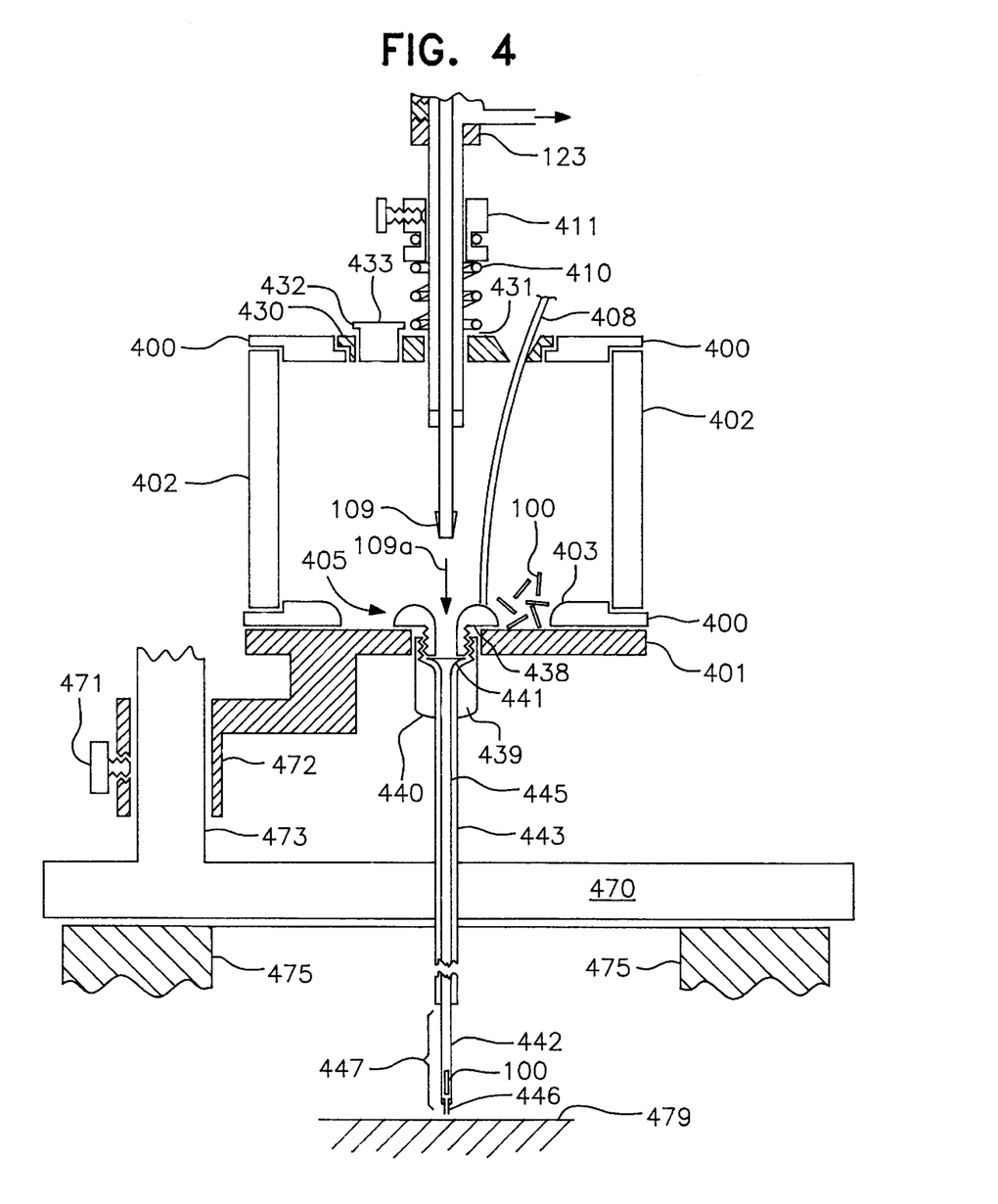
FIG. 4 shows a sectional side view of the spring loaded probe in a radioactive seed assay using a well of any well counter or well calibrator. For simplicity, only part of the supporting rod and ring stand is shown as well as only the top section of the well wall upon which the ring stand rests. There are three major components: 1) a viewable shield housing the radioactive seeds, 2) a TEFLON tube, diameter larger than the seed running from the mini-dome shield to the well bottom of a well counter or well calibrator, and 3) the spring loaded probe which retrieves seeds after each successive assay. After radioactive seeds are introduced into the mini-dome shield, with viewable lead glass plates, a pickup probe is used to manipulate one seed at a time into the top funnel opening of the TEFLON tube assembly. By gravity, the seeds will descend passively through the funnel top of the tube assembly and the funnel rim of the proximal TEFLON tube and will stop at the distal end, which is the probe tip within the TEFLON tube where the opening is restricted at the bottom level of the well.

To accomplish this, three things are needed, a viewable shield housing 400, the radioactive seeds 100, a tube 445 confining a seed (or seeds) running from the shielded housing 400 to the bottom 479 of a well of the well counter or well calibrator and the spring loaded probe. The shielded mini-dome 400, housing the radioactive seeds 100, rests on top of a well wall 475 with a TEFLON tube 445 whose diameter is larger than the seed 100 diameter and which extends from and through the dome platform plate 401 reaching down to the bottom 479 of a well counter or well calibrator.

Using a pickup probe 408 (FIG. 6), one seed 100 at a time is dropped into the TEFLON tube 445 where the activity is read at the bottom 479 of the well. This seed 100 (or seeds) is then retrieved by vacuum force by lowering the spring loaded probe entrance 109 to the funnel 441 and sucking the seed 100 back up into its own directly coupled shielded storage vial 300.

The mini-dome shield 400 is formed by a square tube-shaped metal piece having front and back recesses milled so that front and back lead glass plates 402 fit flush within the square shaped metal housing 400. The top of the square is milled to accept a removable access plate 430. The bottom opening 405 is fitted and fixed to a platform plate 401 with an edge smoothed to form a recessed ring 403 area for holding seeds 100 on the platform plate 401. These seeds are introduced through the side orifice 432 in the top access plate 430 using a dumping funnel 602 and dumping spout 605 after the adjustable platform 472 height adjustment is made.

The adjustable platform 472 is attached to a rod 473 with a lock screw 471 for height adjustment. The rod 473 is fastened to a ring shaped stand 470 fixed on the top of the well wall 475, which is positioned on top of a well counter or well calibrator.

In order to send a seed (or seeds) down the well for activity reading in the TEFLON tube 445, the platform 472 height must be properly adjusted with respect to the fixed ring stand 470 on top of the well wall 475 so that 1) the distal end 442 of the TEFLON tube meets the bottom 479 of the well, and 2) the proximal funnel rim end 441 of the TEFLON tube funnel assembly 440 is laying flat on the platform plate 401.

Figure 6:
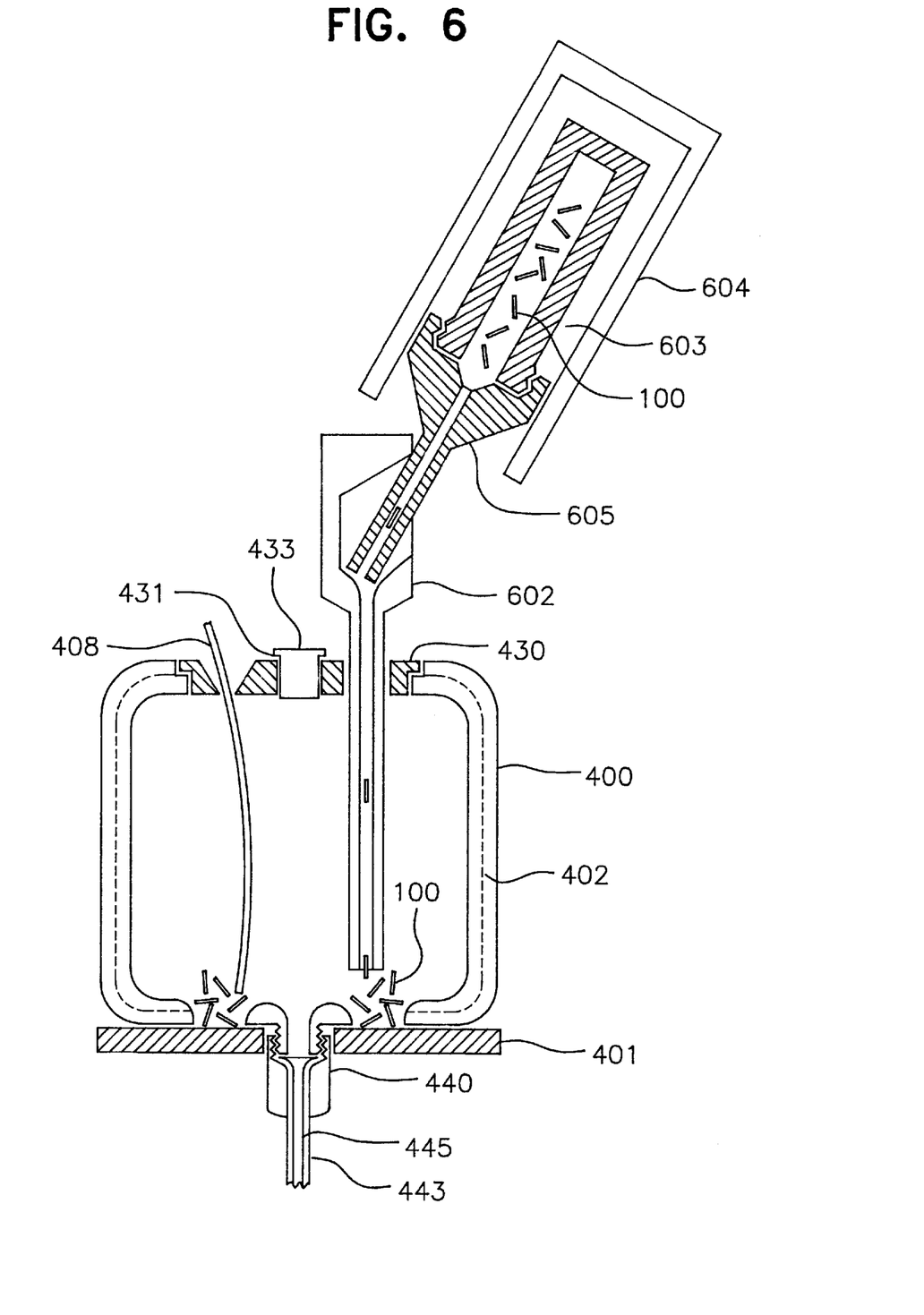
FIG. 6 is a sectional view of a system consisting of a dumping funnel and dumping spout for placing radioactive seeds and spacers onto a platform plate inside the mini-dome shield.

In FIG. 6, after breaking the seal and uncapping the glass vial 603 from the manufacturer containing radioactive seeds, a dumping spout 605 is fastened to the glass vial 603. Next, the dumping funnel 602 is introduced from the top through access plate 430 into the mini-dome shield 400 onto the dome platform recessed ring 403. The seed contents of the glass vial 603 are emptied into the dumping funnel 602 onto the dome platform 401. Both dumping funnel 602 and spout 605 are removed and surveyed (with GM meter) for remaining radioactivity. The radioactive seeds 100 on the platform plate 401 inside the mini-dome shield 400 are now ready for radioactivity assay.

The vacuum pickup probe 408 is inserted into the mini-dome shield 400 and individual seeds 100 are picked up and dropped into the TEFLON tube funnel opening assembly 440. The funnel assembly consists of an externally threaded male top portion 438 with a center bore shaped into a funnel and an internally threaded metal female base portion 439. The assembly top and base sandwich the rim of the TEFLON funnel edge 441 in place making the initial funnel passage smooth. A rigid metallic tube 443, larger than the diameter of the TEFLON tube 445 and affixed to the base portion 439 of the funnel assembly 440, extends down forming a sleeve 443 to straighten the TEFLON tube 445. This metallic sleeve 443 covers all but the exposed tip length 447 of tube 445 necessary for seed activity measurement.

After an activity reading from the well is recorded, any seed(s) 100 inside the TEFLON tube 445 at the bottom 479 of the well must be retrieved back to a shielded storage vial 300. To retrieve the seed(s) from the TEFLON tube 445, a retention spring 410 with lock ring 411 is fitted over the probe entrance 109 on the lower portion of the spring loaded probe. With retention spring 410 and lock ring 411 in place, the spring loaded probe is lowered over and into the mini-dome shield 400 through the central opening access passage 431 of the access plate 430. The retention spring 410 passively keeps the spring loaded probe in suspension directly above and away from the TEFLON tube funnel assembly 440 while the pickup probe 408 is used to place seeds 100 into the TEFLON tube 445 through the TEFLON tube funnel assembly 440. The position of the lock ring 411 on the retention spring 410 is adjusted with respect to the spring loaded probe so that when force is exerted downward on the spring loaded probe, the probe entrance 109 will move down, engage fully with the top of the TEFLON tube funnel assembly 438 (as shown in dotted lines in FIG. 5, in the direction of arrow 109a) and then return, with force when released, to its suspended position avoiding interference for placement of the next seed(s) into the TEFLON tube 445.

Figure 5:
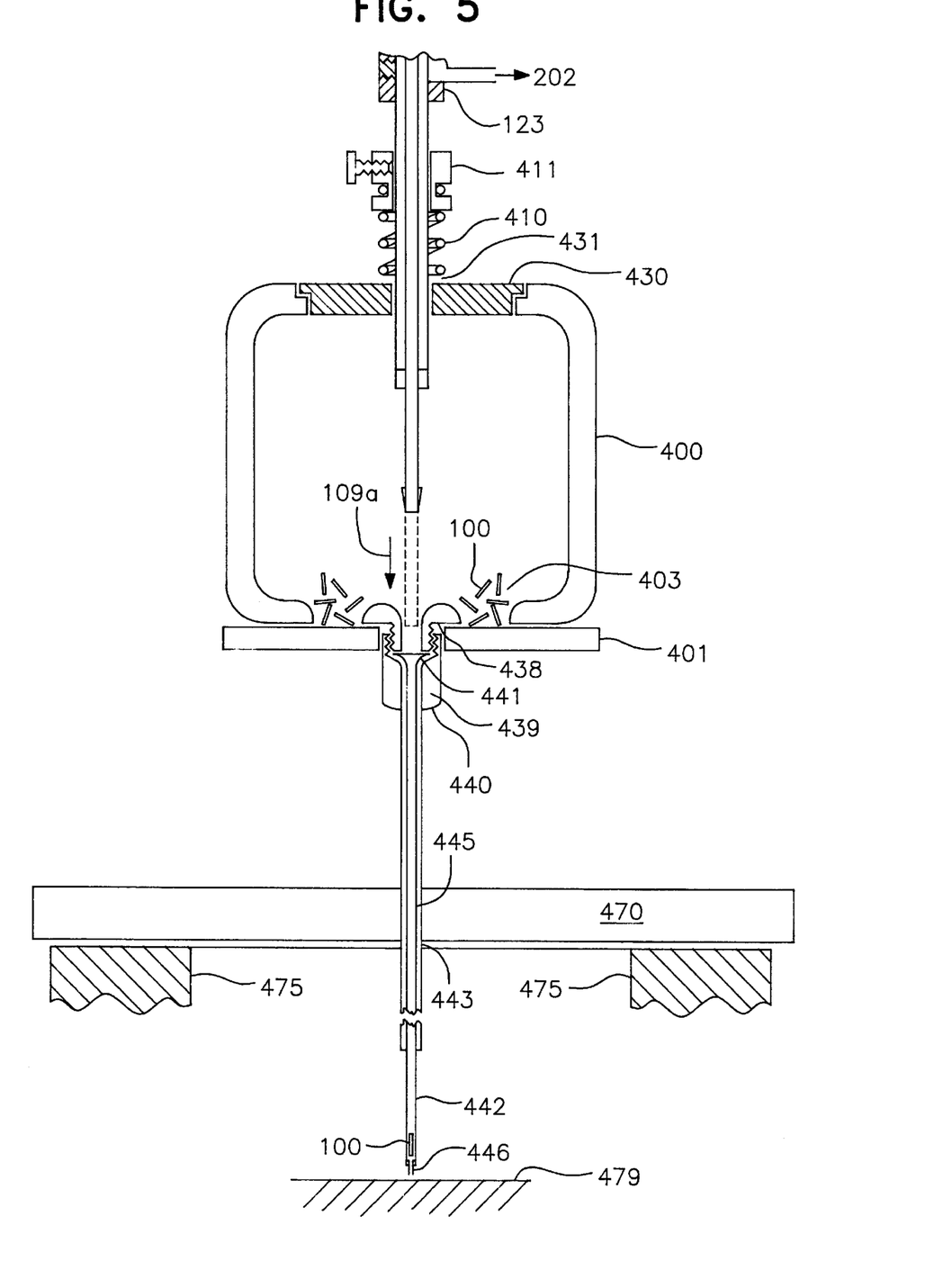
FIG. 5 is a front sectional view of the spring loaded probe used for radioactive assay with the use of a well of a well counter or a well calibrator.

Depressing the spring loaded probe allows the probe entrance 109 to make contact with the TEFLON tube funnel assembly 440. Al the seeds now inside the TEFLON tube 445 will be suctioned up simultaneously from the tip end 446 of the tube 445 back through the spring loaded probe and into the inner nylon basket 303 of the shielded storage vial 300. Normally the sequence of a) dropping a seed or seeds into the well through the TEFLON tube 445, b) recording seed activity in the well, and c) retrieving the seed or seeds 100 back to the shielded vial 300, will be repeated many times since more than a hundred seeds 100 are usually used per patient case. To speed up this process both hands have to be coordinated so that one hand picks up and drops one seed 100 at a time with the pickup probe 408 while the other hand presses down (in the direction of arrow 109*a*) on the spring loaded probe to retrieve the seed(s) 100 back out of the well following recording of activity.

Figures 7A, 7B, 7C:
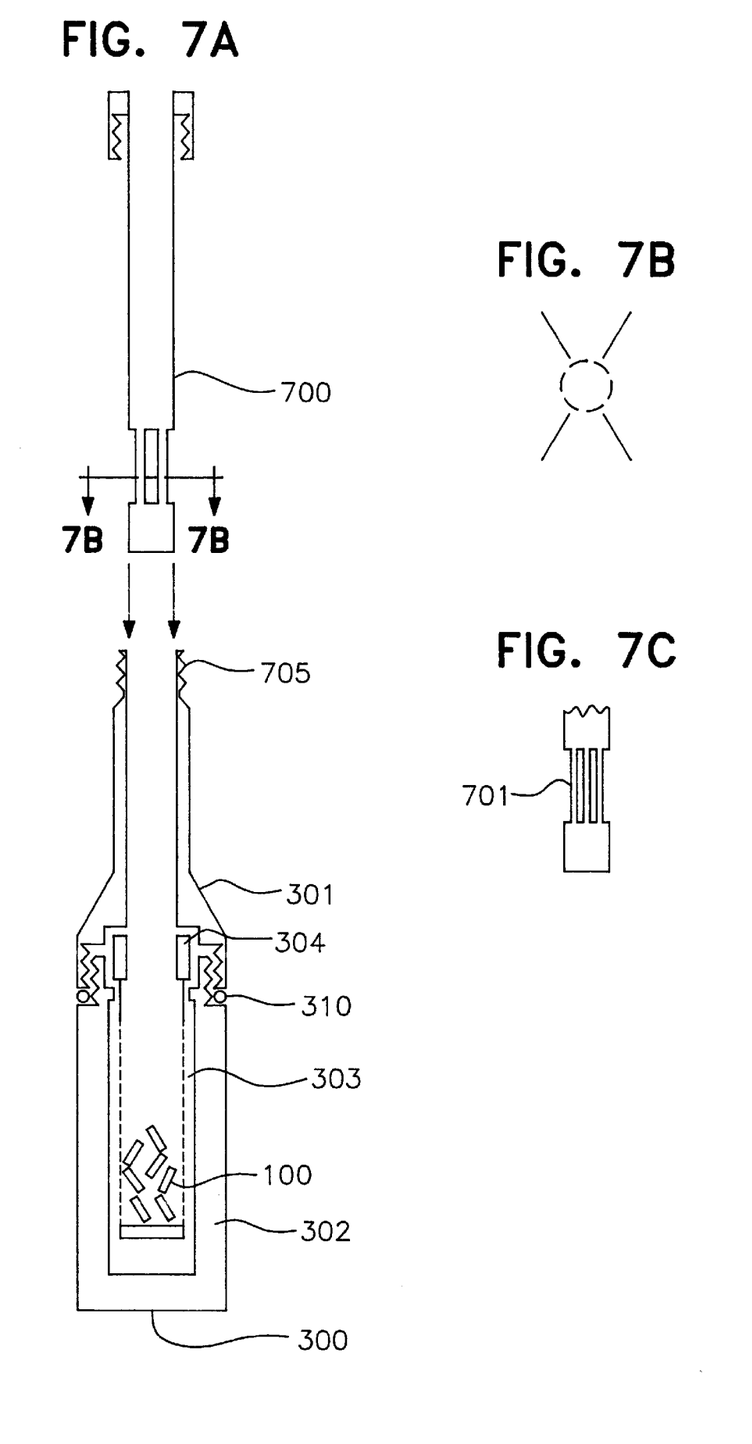

Instead of decoupling the shielded storage vial 300 from the main body of the spring loaded probe and coupling a different shielded vial 300 to pick up any rejected seed(s) 100 or to separate seeds 100 into groups, a second spring loaded probe dedicated as a spare will further speed up the seed assay procedure. All the seeds 100, including those not assayed, are returned to the spring loaded probe and accumulated in the shielded storage vial 300. With the spring loaded probe removed from the mini-dome 400 so that the shielded vial 300 is inverted and sits on its base 302, the shielded vial 300 is uncoupled from the main body of the probe and a vented cap 700 is placed into the shielded vial 300. The vented cap 700 consists of a tube having multiple slits 701 (only six shown) similar to the slits 108 design of the upper portion 106 of the outer tube of the spring loaded probe. The width of each slit 701 is smaller than the diameter of a radioactive seed allowing only steam to pass through and preventing seeds 100 from ever passing through.

An inner high-temperature nylon basket 303 located inside the shielded vial 300 holds the seeds away from the metallic inner wall of the shielded vial 300 for the purpose of preventing condensation or any impurity from accumulating on the seed surface which could result in clumping during the drying cycle of the autoclave. The shielded storage vial 300 with the vented cap secured can now be autoclaved, readying the seeds for needle loading and ultimately for patient seed implantation.

Figures 8A, 8B:
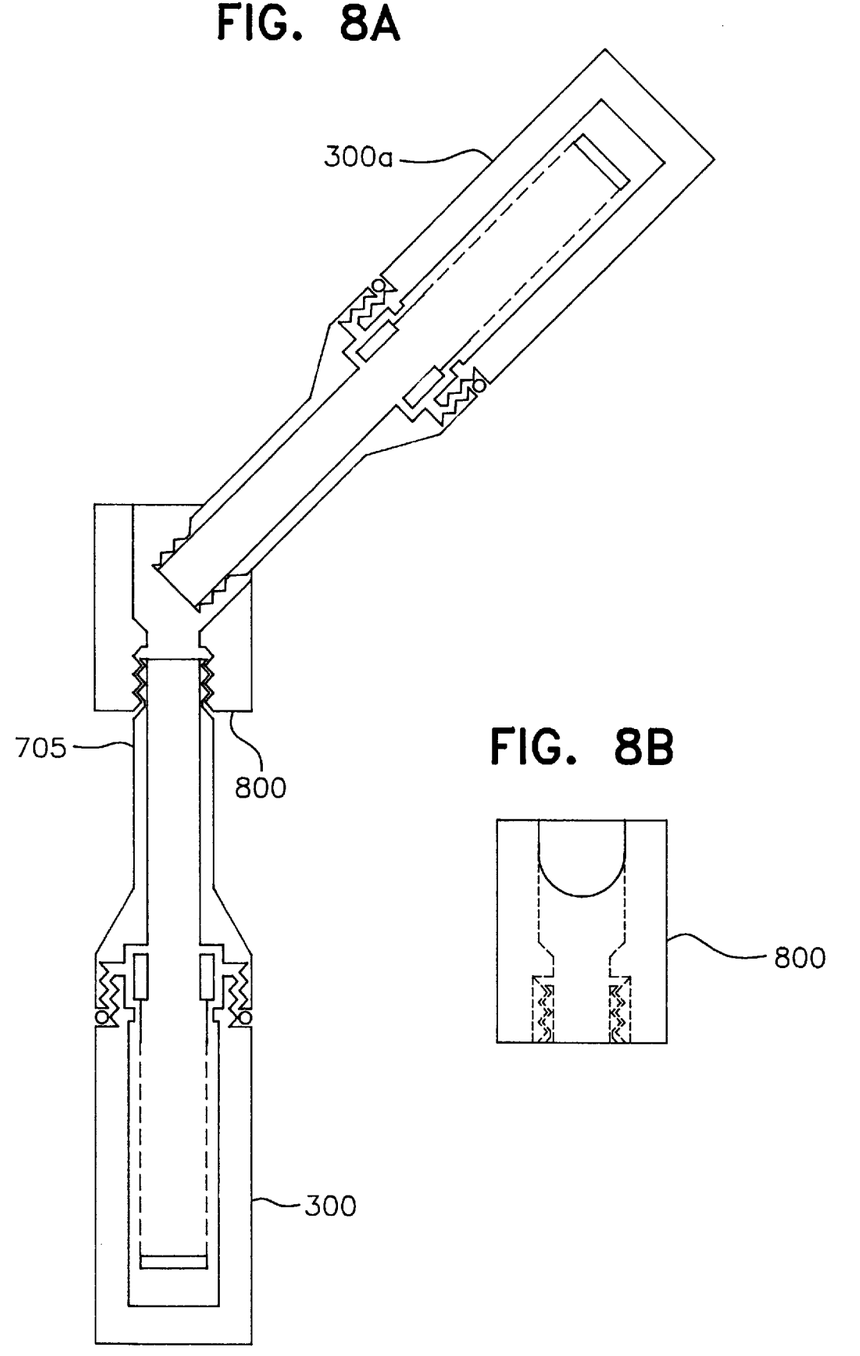

For convenience, seeds can be transferred between shielded storage vials 300. A vial coupler 800 having internal threads can be quickly coupled to the externally threaded vial opening 705. Another vial 300*a*, without vented cap 700, can then be coupled to the first shielded storage vial 300 through the vial coupler 800 in the same manner and the contents emptied from one to the other by inversion of the vial containing 300*a* the seeds 100.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A radioactive seed assay system for use with a well of a well calibrator or a well counter, said system comprising:
   a shield adapted to be mounted on top of the well, and
   a tube extending at one end from said shield and adapted to extend to a bottom of the well at the other end, said tube having a diameter greater than a radioactive seed along substantially its entire length, except at the other end, adapted to be located adjacent to the bottom of the well, said other end having a diameter less than the radioactive seed for retaining the radioactive seed for measurement at the bottom of the well, after which the seed is sucked up said tube from said other end in a direction towards said one end of said tube.

2. A radioactive seed assay system as claimed in claim 1, wherein said tube is surrounded by another tube except at said other end.

3. A radioactive seed assay system as claimed in claim 1, wherein said tube is made of a low friction material made of a compound having elements of low atomic number.

4. A radioactive seed assay system as claimed in claim 1, wherein said shield includes at least one transparent window.

5. A radioactive seed assay system as claimed in claim 1, further including a pickup probe movably mounted on said shield for movement towards said tube for extracting seeds out of said tube in a direction away from said tube.

6. A radioactive seed assay system as claimed in claim 5, wherein said probe includes an opening at one end and a removable shielded storage vial at an opposite end.

7. A radioactive seed assay system as claimed in claim 6, wherein said vial includes a high temperature basket.

8. A radioactive seed assay system as claimed in claim 5, further including an extension tube having an adaptive mouthpiece connected to an open end of said probe through which a vacuum force is transferred from said probe to said extension tube.

9. A method of measuring radioactive seed properties in a well of a well calibrator or a well counter, said method comprising:
   placing an elongated tube into the well,
   feeding a radioactive seed into a proximal end of said tube located externally of the well,
   reading activity of said radioactive seed at a distal end of said tube located adjacent to a bottom of the well, and
   withdrawing said radioactive seed from said distal end to said proximal end of said tube.

10. A method of measuring radioactive seed properties in a well of a well calibrator or a well counter as claimed in claim 9, wherein said proximal end of said tube is located in a radiation shielded compartment.

11. A method of measuring radioactive seed properties in a well of a well calibrator or a well counter as claimed in claim 9, wherein said tube includes a surrounding tube from said proximal end to adjacent to said distal end.

12. A method of measuring radioactive seed properties in a well of a well calibrator or a well counter as claimed in claim 9, wherein a diameter of said tube is greater than a diameter of said radioactive seed from said proximal end to adjacent to said distal end.

13. A method of measuring radioactive seed properties in a well of a well calibrator or a well counter as claimed in claim 10, wherein a probe removes said radioactive seed from said proximal end of said tube.

14. A method of measuring radioactive seed properties in a well or a well calibrator or a well counter as claimed in claim 13, wherein said probe includes a shielded storage vial for radioactive seeds.

15. A radioactive seed assay system for use with a well of a well calibrator or a well counter, said system comprising:
    a shield adapted to be mounted on top of the well,
    a probe mounted on said shield, said probe including an inner tube terminating in a shielded storage vial and said probe extending into an interior of said shield and said probe being movable to a position adjacent to an opening in said shield for leading into the well and for sucking a radioactive seed out of the well and through the inner tube of the probe, into the shielded storage vial.

16. A radioactive seed assay system as claimed in claim 15, wherein an outer tube surrounds said inner tube and includes at least one slit in a sidewall for evacuating air between said inner tube and said outer tube so as to pull a radioactive seed up into one end of the inner tube and into said shielded storage vial located at an opposite end of said inner tube.

17. A radioactive seed assay system as claimed in claim 16, wherein said at least one slit is dimensioned to prevent passage of a radioactive seed through said at least one slit into a sealed gap formed between said inner tube and said outer tube.

18. A radioactive seed assay system as claimed in claim 17, wherein said shielded storage vial is removably mounted on said probe and closed with a vented cap to allow passage of steam and prevent escape of radioactive seeds.

19. A radioactive seed assay system as claimed in claim 15, wherein a retention spring is removably mounted about an exterior of said probe.

20. A radioactive seed assay system as claimed in claim 15, further including an extension tube having an adaptive mouthpiece connected to an open end of said probe through which a vacuum force is transferred from said probe to said extension tube.

* * * * *